(12) United States Patent
Hwang (10) Patent No.: US 12,422,334 B2
(45) Date of Patent: Sep. 23, 2025

(54) OPTICAL BENCH TESTER FOR MULTIFOCAL IOL

(71) Applicant: THE CATHOLIC UNIVERSITY OF KOREA INDUSTRY-ACADEMIC COOPERATION FOUNDATION, Seoul (KR)

(72) Inventor: Hosik Hwang, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 137 days.

(21) Appl. No.: 18/481,858

(22) Filed: Oct. 5, 2023

(65) Prior Publication Data

US 2024/0118166 A1 Apr. 11, 2024

(30) Foreign Application Priority Data

Oct. 6, 2022 (KR) .......................... 10-2022-0127519

(51) Int. Cl.
  *G01M 11/04* (2006.01)
  *G01M 11/02* (2006.01)
  *A61F 2/16* (2006.01)

(52) U.S. Cl.
  CPC ........ *G01M 11/04* (2013.01); *G01M 11/0214* (2013.01); *A61F 2/1618* (2013.01)

(58) Field of Classification Search
  CPC ............. G01M 11/04; G01M 11/0264; G01M 11/0214; A61F 2/1618; A61B 3/10; A61B 3/032; A61B 3/0025
  See application file for complete search history.

(56) References Cited

U.S. PATENT DOCUMENTS 5,500,732 A * 3/1996 Ebel .................... B29D 11/0098
  356/124
5,652,640 A * 7/1997 Schneider ................. A61F 2/16
  351/205
(Continued)

FOREIGN PATENT DOCUMENTS

| CN | 211944279 U | 11/2020 |
| JP | 2012-068551 A | 4/2012 |
| KR | 10-2132214 B1 | 7/2020 |

OTHER PUBLICATIONS

Harou "Ophthalmic Device", Jun. 8, 2017, JP 2017102293 A (Year: 2017).*

(Continued)

*Primary Examiner* — Sang H Nguyen
(74) *Attorney, Agent, or Firm* — Knobbe, Martens, Olson & Bear, LLP (57) ABSTRACT

An optical bench tester for a multifocal intraocular lens is disclosed. An optical bench tester for a multifocal intraocular lens according to an aspect of the present disclosure may include a resolution test chart; a plurality of optical systems that refract images irradiated from the resolution test chart; an electrically driven liquid lens unit provided at the rear of the optical system to control the refraction of light passing through; a model eye having a multifocal intraocular lens on which light transmitting through the electrically driven liquid lens unit is incident; a camera that captures light transmitted through the model eye; and a control unit that controls the electrically driven liquid lens unit to control the refractive index of the electrically driven liquid lens unit, and calculates a defocus curve by analyzing images captured through the camera.

7 Claims, 6 Drawing Sheets

(56) References Cited

U.S. PATENT DOCUMENTS

| | | | |
|---|---|---|---|
| 6,314,199 B1* | 11/2001 | Hofer | G01N 21/88 |
| | | | 382/141 |
| 2001/0035949 A1 | 11/2001 | Epstein et al. | |
| 2008/0137076 A1* | 6/2008 | Clements | G01M 11/0207 |
| | | | 356/124 |
| 2009/0303465 A1* | 12/2009 | Clements | G01M 11/0242 |
| | | | 356/124 |
| 2011/0317277 A1 | 12/2011 | Pugh et al. | |
| 2014/0160436 A1* | 6/2014 | Kasthurirangan | A61B 3/10 |
| | | | 351/239 |
| 2017/0016771 A1* | 1/2017 | Koresko | G01J 5/53 |
| 2021/0165207 A1* | 6/2021 | Peyman | A61F 2/1651 |
| 2023/0371885 A1* | 11/2023 | Uthoff | A61B 5/0077 |

OTHER PUBLICATIONS

Masanori et al "Apparatus and Method of Inspecting Intraocular Lens", Mar. 18, 2010, JP2010 060472A (Year: 2010).*

Yoshiaki et al "Lens Meter", Jan. 25, 1994, JP H0618363 A (Year: 1994).*

Office Action issued in Korean Patent Application No. 10-2022-0127519 dated Jun. 12, 2024 in 10 pages.

* cited by examiner

OPTICAL BENCH TESTER FOR MULTIFOCAL IOL

CROSS-REFERENCE TO RELATED APPLICATION

This application claims priority to and the benefit of Korean Patent Application No. 10-2022-0127519, filed on Oct. 6, 2022, the disclosure of which is incorporated herein by reference in its entirety.

TECHNICAL FIELD

The present disclosure relates to an optical bench tester for a multifocal intraocular lens (IOL), and more specifically, to an optical bench tester for a multifocal intraocular lens with minimized size and volume.

BACKGROUND

The use of multifocal intraocular lenses is increasing day by day due to aging and other reasons. After inserting a multifocal intraocular lens into a patient, a survey is conducted to evaluate the multifocal intraocular lens, including distance visual acuity, near visual acuity, satisfaction, and recommendation.

Meanwhile, one of the most important data that shows the function of a multifocal intraocular lens is the defocus curve. This indicates how one's visual acuity is at far, intermediate, and near distances.

The disclosure of this section is to provide background information relating to the present disclosure. Applicant does not admit that any information contained in this section constitutes prior art.

SUMMARY

Technical Tasks

To obtain the defocus curve of a multifocal intraocular lens in the eyes of a patient implanted with a multifocal intraocular lens, repeated visual acuity measurements are required.

However, this is cumbersome for patients and examiners, and even at the same defocus, visual acuity deviation is severe for each patient, making it inaccurate.

Therefore, there is a need to develop an apparatus to objectively determine the characteristics of the multifocal intraocular lens to be implanted before implanting it into a patient.

The present disclosure is directed to providing an optical bench tester for a multifocal intraocular lens that can obtain a defocus curve of a model eye into which a multifocal intraocular lens to be implanted in a patient is inserted before implanting it in the patient.

The technical tasks of the present disclosure are not limited to the technical tasks mentioned above, and other technical tasks not mentioned will be clearly understood by those of ordinary skill in the art from the following description.

Technical Solution

According to an aspect of the present disclosure, an optical bench tester for a multifocal intraocular lens is provided, including a resolution test chart; a plurality of optical systems that refract images irradiated from the resolution test chart; an electrically driven liquid lens unit provided at the rear of the optical system to control the refraction of light passing through; a model eye having a multifocal intraocular lens on which light transmitting through the electrically driven liquid lens unit is incident; a camera that captures light transmitted through the model eye; and a control unit that controls the electrically driven liquid lens unit to control the refractive index of the electrically driven liquid lens unit, and calculates a defocus curve by analyzing images captured through the camera.

The model eye may include a housing filled with physiological saline solution; a multifocal intraocular lens placed within the housing; and a transparent window formed in the housing to transmit light incident on the multifocal intraocular lens and light passing through the multifocal intraocular lens.

The optical bench tester for a multifocal intraocular lens may further include a model eye holder that detachably mounts the model eye.

The model eye may have a first rail formed on both sides of the housing along a direction perpendicular to the direction in which light is projected, and the model eye holder may include a first support base supporting the housing of the model eye by contacting a side of the housing of the model eye; and a first fork portion extending from the first support base to be inserted into the first rail on both sides of the housing of the model eye, respectively.

A first coupling groove may be formed in the first rail, and a first coupling protrusion may be formed in the first fork portion so that the model eye is elastically inserted into the first coupling groove of the first rail when the model eye is coupled to the correct position of the model eye holder.

The optical bench tester for a multifocal intraocular lens may further include an offset lens unit that is provided at the rear of the electrically driven liquid lens unit and refracts light refracted by the electrically driven liquid lens unit to diffuse or concentrate the light, thereby moving the refraction range of the light; and an offset lens holder for mounting the offset lens unit in a detachable and exchangeable manner.

The offset lens unit may have a second rail formed on both sides along a direction perpendicular to the direction in which light is projected, and the offset lens holder may include a second support base supporting the offset lens unit by contacting a side of the offset lens unit; and a second fork portion extending from the second support base to be inserted into the second rail on both sides of the offset lens unit, respectively.

The electrically driven liquid lens unit may be a convex lens whose refractive index is adjusted, and the offset lens unit may be a concave lens.

Advantageous Effects

According to the above configuration, the optical bench tester for a multifocal artificial lens according to the present disclosure can obtain a defocus curve before implanting a model eye into which a multifocal intraocular lens to be implanted into a patient is inserted is implanted in a patient, thereby maximizing the effectiveness of surgery and patient satisfaction.

In addition, accuracy can be improved by objectively evaluating the defocus curve of a multifocal intraocular lens using automated equipment rather than having the patient evaluate it on their own.

Advantageous effects of the present disclosure are not limited to the above-described effects, and should be understood to include all effects that can be inferred from the

DETAILED DESCRIPTION OF EMBODIMENTS

Hereinafter, embodiments of the present disclosure will be described in detail so that those of ordinary skill in the art can readily implement the present disclosure with reference to the accompanying drawings. The present disclosure may be embodied in many different forms and is not limited to the embodiments set forth herein. In the drawings, parts unrelated to the description are omitted for clarity of description of the present disclosure, and throughout the specification, same or similar reference numerals denote same elements.

Terms and words used in the present specification and claims should not be construed as limited to their usual or dictionary definition, and they should be interpreted as a meaning and concept consistent with the technical idea of the present disclosure based on the principle that inventors may appropriately define the terms and concept in order to describe their own disclosure in the best way.

Accordingly, the embodiments described in the present specification and the configurations shown in the drawings correspond to embodiments of the present disclosure, and do not represent all the technical idea of the present disclosure, so the configurations may have various examples of equivalent and modification that can replace them at the time of filing the present disclosure.

It should be understood that the terms "comprise" or "have" or the like when used in this specification, are intended to describe the presence of stated features, integers, steps, operations, elements, components and/or a combination thereof but not preclude the possibility of the presence or addition of one or more other features, integers, steps, operations, elements, components, or a combination thereof.

The presence of an element in/on "front", "rear", "upper or above or top" or "lower or below or bottom" of another element includes not only being disposed in/on "front", "rear", "upper or above or top" or "lower or below or bottom" directly in contact with other elements, but also cases in which another element being disposed in the middle, unless otherwise specified. In addition, unless otherwise specified, that an element is "connected" to another element includes not only direct connection to each other but also indirect connection to each other.

Hereinafter, an optical bench tester for a multifocal intraocular lens according to an embodiment of the present disclosure will be described in detail with reference to the drawings.

Figure 1:
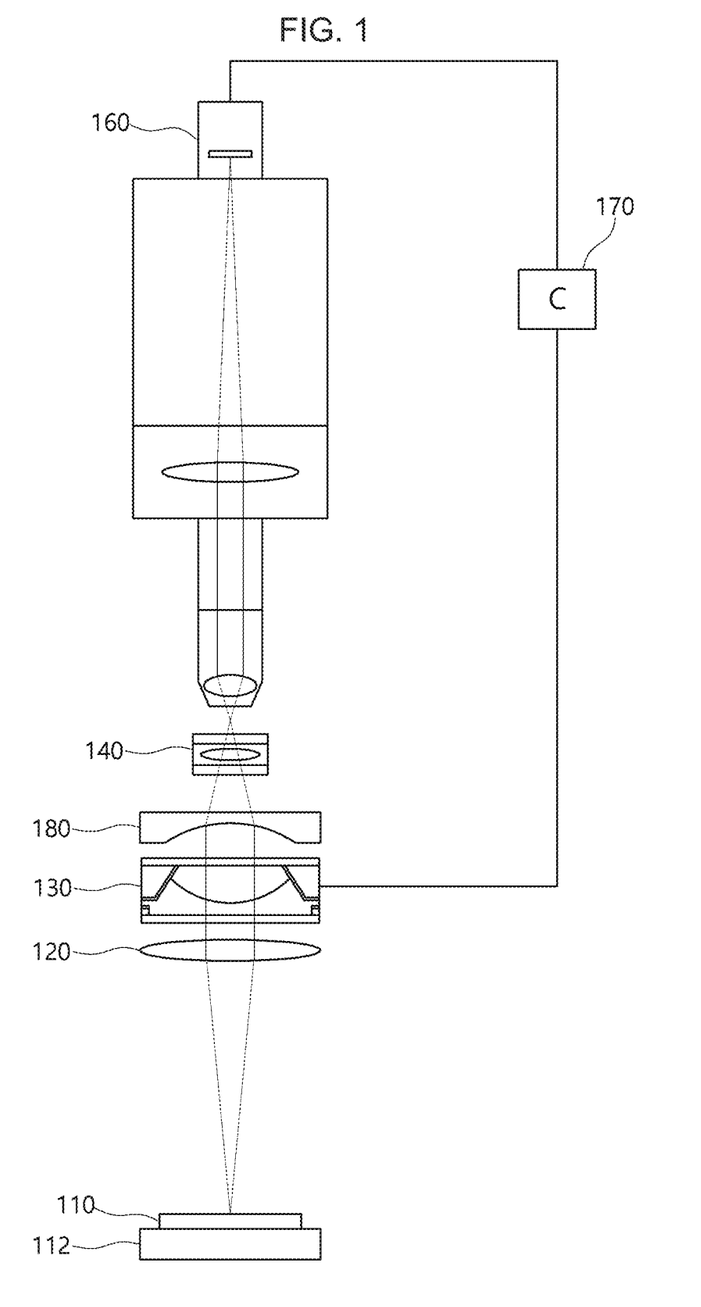
FIG. 1 is a diagram illustrating an optical bench tester for a multifocal intraocular lens according to an embodiment of the present disclosure.

FIG. 1 is a diagram illustrating an optical bench tester 100 for a multifocal intraocular lens according to the present embodiment.

As shown in FIG. 1, the optical bench tester 100 for a multifocal intraocular lens according to the present embodiment may include a resolution test chart 110, an optical system 120, an electrically driven liquid lens unit 130, a model eye 140, a camera 160, and a control unit 170.

The resolution test chart 110 is a chart in which shapes or letters or the like are displayed at various sizes or intervals.

The resolution test chart 110 may have its own light source 112 so that the shapes or letters are emitted, or external light may be reflected so that the shapes or letters are identified. In the present embodiment, the resolution chart will be described by taking the 1951 United States Air Force resolution test chart as an example. In this case, green light, which has less influence on the human body or model eye 140, may be applied as the light source 112.

The optical system 120 includes or consists of at least one lens and is configured to appropriately refract light irradiated or reflected from the resolution chart 110.

The electrically driven liquid lens unit 130 is provided at the rear of the optical system 120 and is a lens whose refractive index changes by electrical control.

Figure 2:
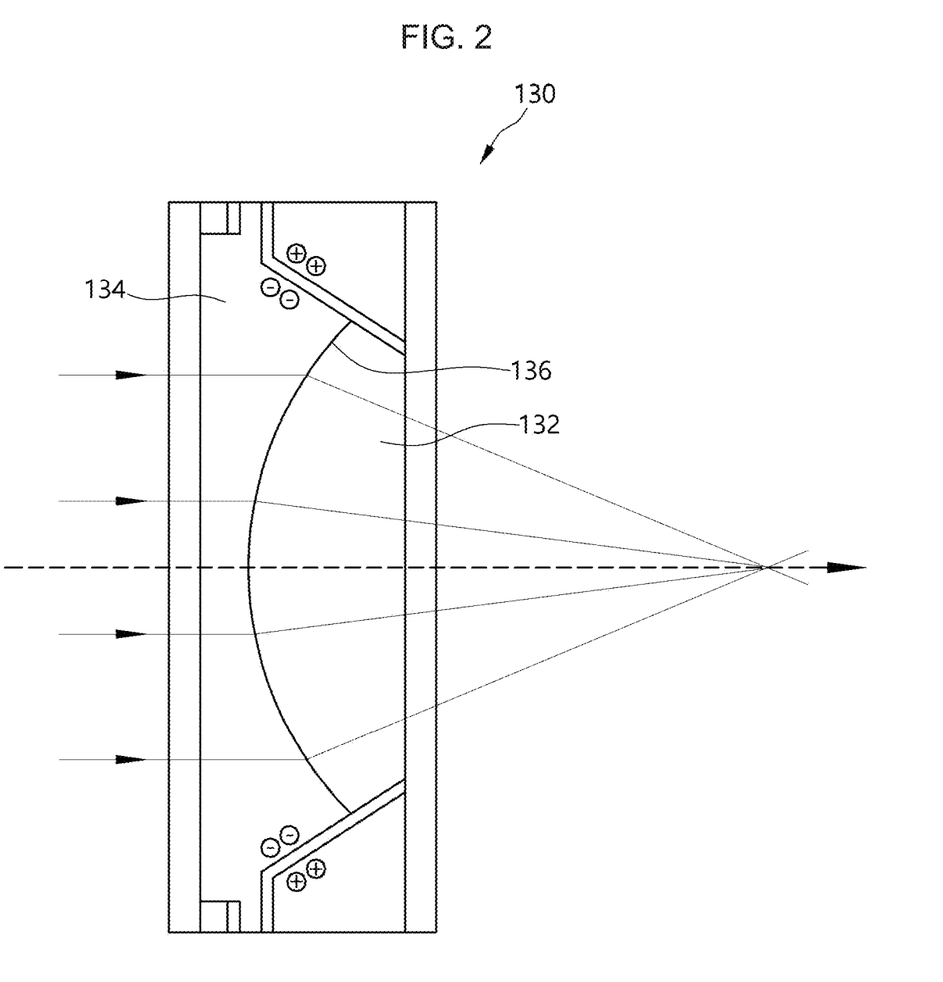
FIG. 2 is a diagram illustrating an electrically driven liquid lens unit applied to an optical bench tester for a multifocal intraocular lens according to an embodiment of the present disclosure.

As shown in FIG. 2, the electrically driven liquid lens unit 130 contains two layers of immiscible liquids 132 and 134, such as water and oil, enclosed between a pair of transparent windows, one of which may be a non-conductive liquid, and the other may be a conductive aqueous solution.

When electric power is applied to an interface 136 between the two liquids, the curvature, or focal length, of the interface 136 between the two liquids changes within a short period of time. Additionally, when a weaker electric power is applied, the curvature of the interface 136 between the two liquids decreases, and when a stronger electric power is applied, the curvature of the interface 136 between the two liquids increases. Additionally, the interface 136 between the two liquids may function as a lens.

Therefore, by controlling the electric power applied to the interface 136 between the two liquids, the curvature of the interface 136 between the two liquids can be controlled, and through this, the focal length can be controlled, thereby controlling the refraction of the light passing through.

In other words, the refraction and focal length of light can be adjusted as a configuration of the electrically driven liquid lens unit 130 without adjusting the spacing of a plurality of lenses, and thus, the configuration and volume can be further simplified.

Light passing through the electrically driven liquid lens unit 130 is incident on the model eye 140, and the model eye may be provided with a multifocal intraocular lens 144 therein to be implanted into a patient.

Figure 3:
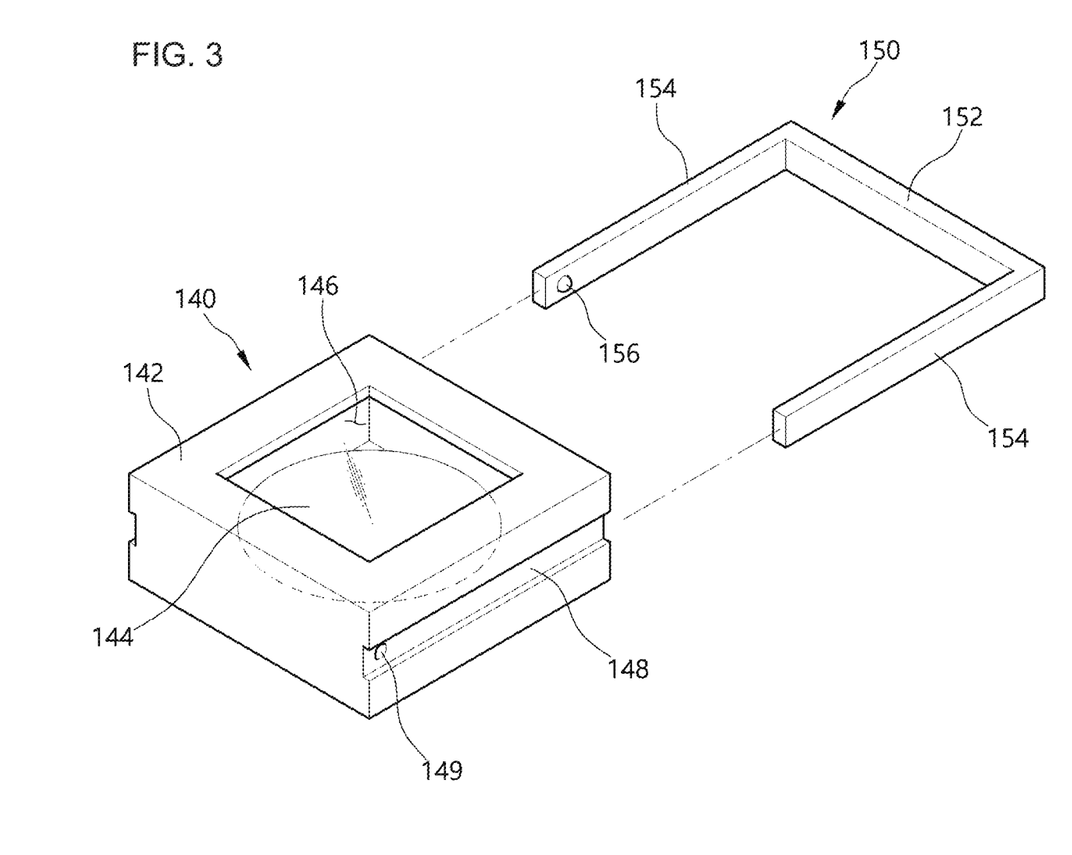
FIG. 3 is a diagram illustrating a model eye and a model eye holder applied to an optical bench tester for a multifocal intraocular lens according to an embodiment of the present disclosure.

As shown in FIG. 3, the model eye 140 may include a housing 142, a multifocal intraocular lens 144, and a transparent window 146.

The housing 142 forms a space inside which the multifocal intraocular lens 144 is placed, and may be filled with physiological saline solution.

The multifocal intraocular lens 144 is a multifocal intraocular lens or an object of the same type to be implanted in a patient, and is placed inside the housing 142 and may float in the physiological saline solution filled in the housing 142.

The transparent window 146 may be formed in the housing 142 to transmit light incident on the multifocal intraocular lens 144 and light passing through the multifocal intraocular lens 144.

In addition, the camera 160 is provided to photograph the light transmitted through the model eye 140, and the control unit 170 may control the refractive index of the electrically driven liquid lens unit 130 to generate quantified defocus by controlling the electrically driven liquid lens unit 130, and may calculate a defocus curve by analyzing the image captured through the camera 160.

Meanwhile, the model eye 140 may be provided to be detachable.

The multifocal intraocular lens 144 applied to each patient may be different, and since the defocus curve may need to be measured for each applied multifocal intraocular lens 144, the model eye 140 may be provided for replacement.

Accordingly, a model eye holder 150 may be provided to detachably mount the model eye 140.

Figure 4:
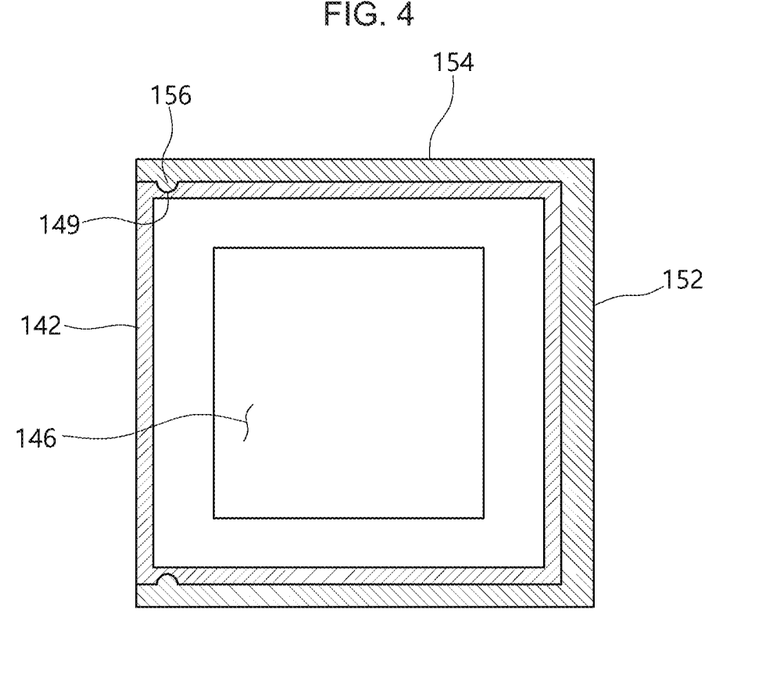
FIG. 4 is a diagram illustrating a model eye applied to an optical bench tester for a multifocal intraocular lens according to an embodiment of the present disclosure mounted on a model eye holder.

In this case, the model eye 140 may have a first rail 148 formed on both sides of the housing 142 in a direction perpendicular to the direction in which light passes through. Additionally, the model eye 140 may include a first support base 152 and a first fork portion 154.

The first support base 152 may be provided to support the housing 142 of the model eye 140 by contacting a side of the housing 142 of the model eye 140.

In addition, the first fork portion 154 may extend from the first support base 152 to slide and be inserted into the first rail 148 on both sides of the housing 142 of the model eye 140, respectively.

In addition, a first coupling groove is formed in the first rail 148, and a first coupling protrusion 156 may be formed in the first fork portion 154 so that the model eye 140 is elastically inserted into the first coupling groove 149 of the first rail 148 when the model eye 140 is coupled to the correct position of the model eye holder 150.

The first fork portion 154 may be formed of an elastic material so that the first coupling protrusion 156 is elastically inserted into the first coupling groove 149.

Therefore, when the first fork portion 154 is inserted into the first rail 148 and the first coupling protrusion 156 is inserted into the first coupling groove 149, a side of the housing 142 is supported by the first support base 152 so that the model eye 140 can be firmly mounted.

Figure 5:
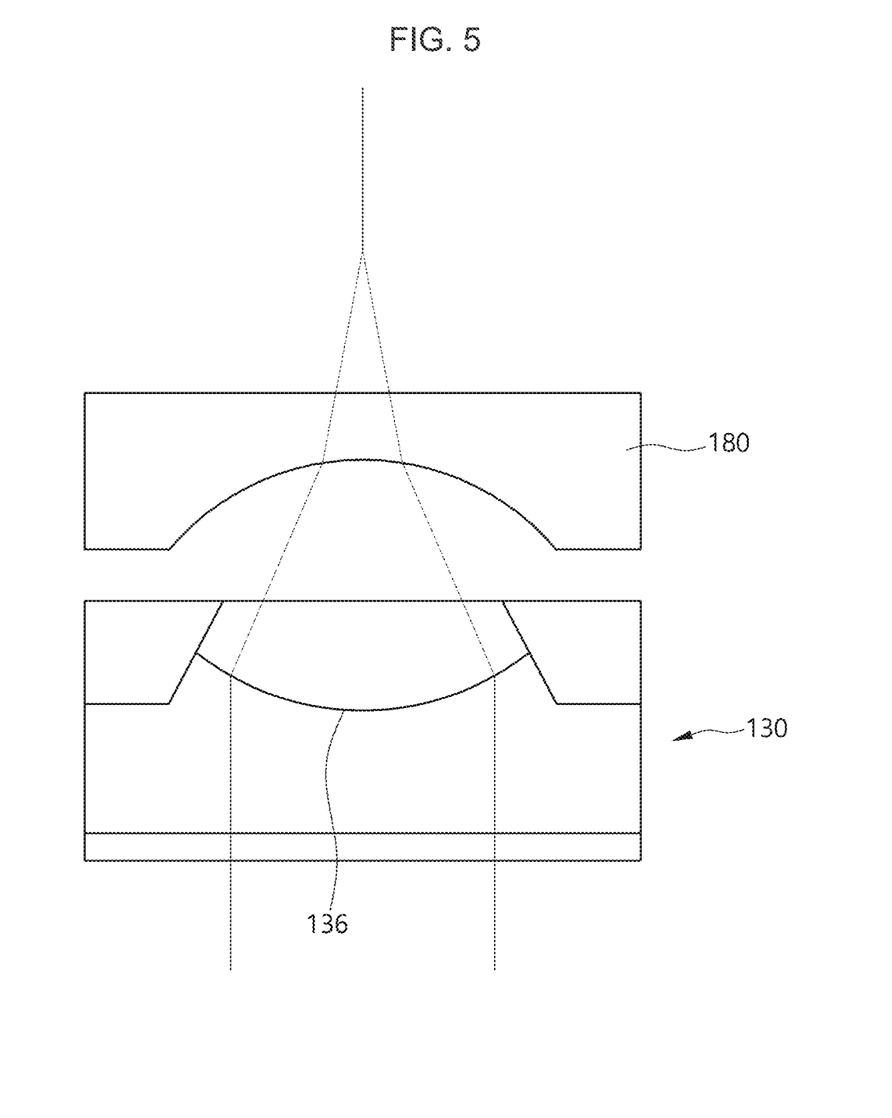
FIG. 5 is a diagram illustrating an electrically driven liquid lens unit and an offset lens unit of an optical bench tester for a multifocal intraocular lens according to an embodiment of the present disclosure.

Meanwhile, the electrically driven liquid lens unit 130 has a limited curvature adjustment range and cannot implement reverse curvature. However, in order to implement defocus curves for various types of multifocal intraocular lenses 144 applied to patients, it may be necessary to implement a wide adjustment range of focal length and, if necessary, also a situation in which reverse curvature is applied.

Figure 6:
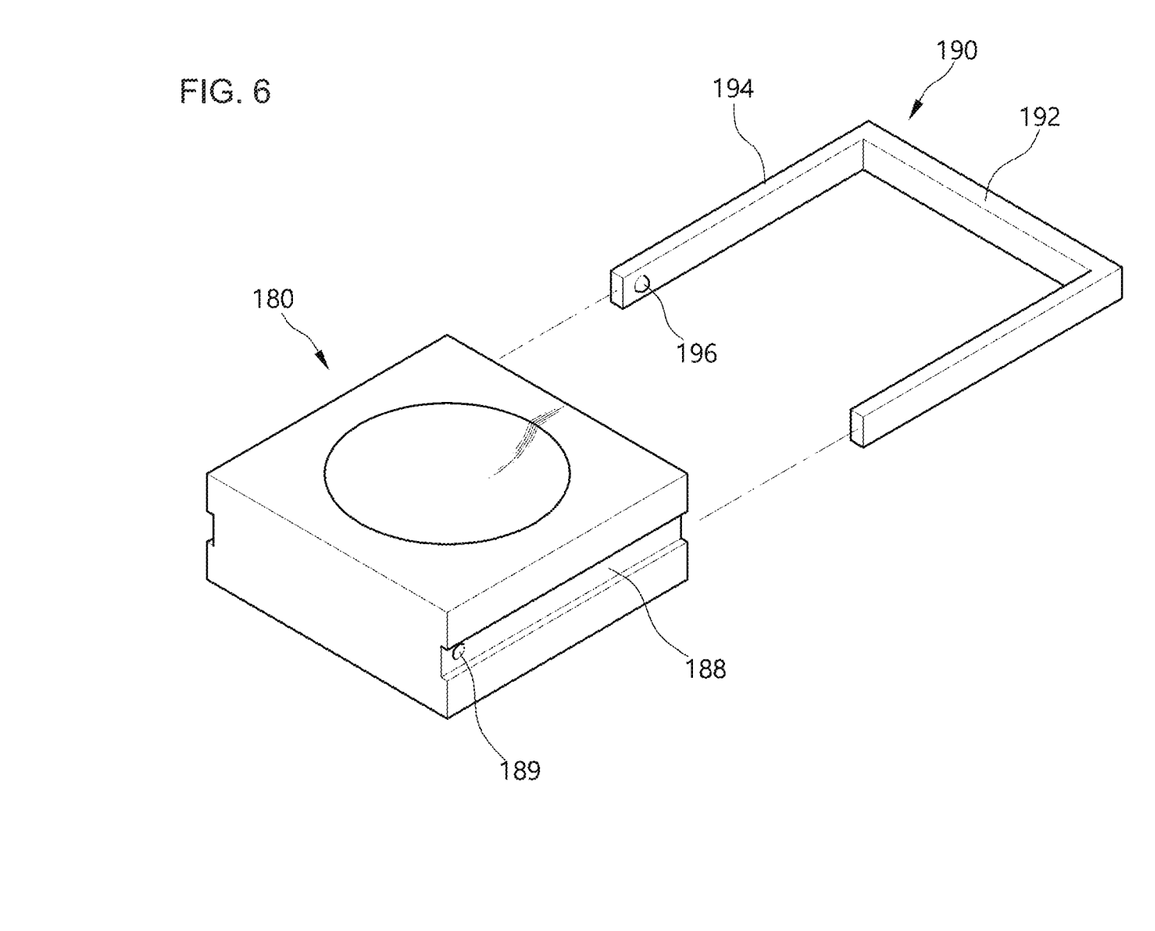
FIG. 6 is a diagram illustrating an offset lens unit and an offset lens holder applied to an optical bench tester for a multifocal intraocular lens according to an embodiment of the present disclosure.

Therefore, the optical bench tester 100 for a multifocal intraocular lens according to the present embodiment may include an offset lens unit 180 that is provided at the rear of the electrically driven liquid lens unit 130 and refracts the light refracted by the electrically driven liquid lens unit 130 to diffuse or concentrate the light, thereby moving the refraction range of the light; and an offset lens holder 190 for mounting the offset lens unit 180 to be detachable and exchangeable.

Here, moving the refraction range of light may mean that the size of the width of the range where light is refracted is constant, but the value of the range where light is refracted is moved.

For example, if the refraction range adjusted by the electrically driven liquid lens unit 130 is 0 to +5 diopters, the refraction range adjusted through the offset lens unit 180 may be −4 to +1 diopters.

In the present embodiment, it is described as an example that the electrically driven liquid lens unit 130 is a convex lens whose refractive index is adjusted, and the offset lens unit 180 is a concave lens, but the present disclosure is not necessarily limited thereto.

For example, the electrically driven liquid lens unit 130 and the offset lens unit 180 may both be convex lenses or concave lenses, or the electrically driven liquid lens unit 130 may be a concave lens, and the offset lens unit 180 may be a convex lens.

Therefore, the offset lens unit 180 with an appropriate refraction range can be selected and mounted according to the refraction range of the electrically driven liquid lens unit 130 and the refraction range to be implemented.

Meanwhile, in order to achieve a wider adjustment range of focal length, an offset lens holder 190 may be provided to mount the offset lens unit 180 in a detachable and exchangeable manner.

In this case, a second rail 188 may be formed on both sides of the offset lens unit 180 along a direction perpendicular to the direction in which light is projected. Additionally, the offset lens holder 190 may include a second support base 192 and a second fork portion 194. The second support base 192 may be provided to support the offset lens unit 180 by contacting a side of the offset lens unit 180.

Additionally, the second fork portion 194 may extend from the second support base 192 to slide and be inserted into the second rail 188 on both sides of the offset lens unit 180, respectively.

In addition, a second coupling groove is formed in the second rail 188, and a second coupling protrusion 196 may be formed in the second fork portion 194 so that the offset lens unit 180 is elastically inserted into the second coupling groove 189 of the second rail 188 when the offset lens unit 180 is coupled to the correct position of the offset lens holder 190.

The second fork portion 194 may be formed of an elastic material so that the second coupling protrusion 196 is elastically inserted into the second coupling groove 189.

Therefore, when the second fork portion 194 is inserted into the second rail 188 and the second coupling protrusion 196 is inserted into the second coupling groove 189, a side of the offset lens unit 180 is supported by the second support base 192 so that the offset lens unit 180 can be firmly mounted.

Although embodiments of the present disclosure have been described, the idea of the present disclosure is not limited to the embodiments set forth herein. Those of ordinary skill in the art who understand the idea of the present disclosure may easily propose other embodiments through supplement, change, removal, addition, etc. of elements within the same idea, but the embodiments will be also within the idea scope of the present disclosure.

DESCRIPTION OF SYMBOLS

| | |
|---|---|
| 100: optical bench tester for a multifocal intraocular lens | |
| 110: resolution test chart | 120: optical system |
| 130: electrically driven liquid lens unit | 132: interface |
| 140: model eye | 142: housing |
| 144: multifocal intraocular lens | 146: window |
| 150: model eye holder | 160: camera |
| 170: control unit | 180: offset lens unit |
| 190: offset lens holder | |

What is claimed is:

1. An optical bench tester for a multifocal intraocular lens, comprising:
    a resolution test chart;
    at least one optical system that refracts images irradiated from the resolution test chart;
    an electrically driven liquid lens unit provided at the rear of the at least one optical system to control the refraction of light passing through;
    a model eye having a multifocal intraocular lens on which light transmitting through the electrically driven liquid lens unit is incident;
    a camera that captures light transmitted through the model eye;
    an offset lens unit that is provided at the rear of the electrically driven liquid lens unit and refracts light refracted by the electrically driven liquid lens unit to diffuse or concentrate the light, thereby moving the refraction range of the light;
    an offset lens holder for mounting the offset lens unit in a detachable and exchangeable manner; and
    a control unit that controls the electrically driven liquid lens unit to control the refractive index of the electrically driven liquid lens unit, and calculates a defocus curve by analyzing images captured through the camera.

2. The optical bench tester for a multifocal intraocular lens of claim 1, wherein the model eye comprises:
    a housing filled with physiological saline solution;
    the multifocal intraocular lens placed within the housing; and
    a transparent window formed in the housing to transmit light incident on the multifocal intraocular lens and light passing through the multifocal intraocular lens.

3. The optical bench tester for a multifocal intraocular lens of claim 2, further comprising a model eye holder that detachably mounts the model eye.

4. The optical bench tester for a multifocal intraocular lens of claim 3,
    wherein the model eye has a first rail formed on both sides of the housing along a direction perpendicular to the direction in which light is projected, and
    the model eye holder comprises:
        a first support base supporting the housing of the model eye by contacting a side of the housing of the model eye; and
        a first fork portion extending from the first support base to be inserted into the first rail on both sides of the housing of the model eye, respectively.

5. The optical bench tester for a multifocal intraocular lens of claim 4,
    wherein a first coupling groove is formed in the first rail, and
    a first coupling protrusion is formed in the first fork portion so that the model eye is elastically inserted into the first coupling groove of the first rail when the model eye is coupled to the correct position of the model eye holder.

6. The optical bench tester for a multifocal intraocular lens of claim 1,
    wherein the offset lens unit has a second rail formed on both sides along a direction perpendicular to the direction in which light is projected, and
    the offset lens holder comprises:
        a second support base supporting the offset lens unit by contacting a side of the offset lens unit; and
        a second fork portion extending from the second support base to be inserted into the second rail on both sides of the offset lens unit, respectively.

7. The optical bench tester for a multifocal intraocular lens of claim 1,
    wherein the electrically driven liquid lens unit is a convex lens whose refractive index is adjusted, and
    the offset lens unit is a concave lens.

* * * * *